United States Patent [19]
Anschutz

[11] Patent Number: 5,860,985
[45] Date of Patent: Jan. 19, 1999

[54] OPHTHALMIC INSTRUMENT FOR CATARACT SURGERY

[76] Inventor: Till Rainer Anschutz, Alte Wein Str. 5, 76593 Gersbach, Germany

[21] Appl. No.: 733,497

[22] Filed: Oct. 18, 1996

[51] Int. Cl.[6] .................................................. A61F 09/00
[52] U.S. Cl. ........................ 606/107; 606/205; 606/207; 30/186
[58] Field of Search ..................... 606/107, 205, 606/206, 207, 210, 211, 160, 161, 166; 30/186, 191, 115, 116, 117, 304

[56] References Cited

U.S. PATENT DOCUMENTS

| | | | |
|---|---|---|---|
| 2,709,298 | 5/1955 | Mater | 30/117 |
| 2,740,195 | 4/1956 | Stadeli et al. | 30/115 |
| 3,116,770 | 1/1964 | Tanuma | 30/117 |
| 3,404,677 | 10/1968 | Springer | 606/206 |
| 3,916,909 | 11/1975 | Kletschka et al. | 606/211 |
| 4,300,564 | 11/1981 | Furihata | 606/207 |
| 4,960,418 | 10/1990 | Tennant | 606/206 |
| 5,002,554 | 3/1991 | Korber | 606/207 |
| 5,269,790 | 12/1993 | Funatsu | 606/205 |

*Primary Examiner*—Richard J. Apley
*Assistant Examiner*—Justine R. Yu
*Attorney, Agent, or Firm*—Oppenheimer Wolff & Donnelly LLP

[57] ABSTRACT

An ophthalmic instrument for removal of the natural cataractogenious lens includes a distal end portion configured to be received through a small incision into the anterior capsule of the eye. This distal end portion includes a pair of opposed jaw portions movable by manual manipulation of a pair of handle portions defined on a proximal portion of the instrument. One of the opposed jaw portions is perforate to more effectively fracture the cataractogenious lens. One of the opposed jaws may include a conduit allowing irrigation liquid to be supplied into the eye, while the other opposed jaw may include a conduit allowing aspiration of irrigation liquid and fractured particles of the lens. Because the small incision may fit relatively tightly around the instrument, fluid loss from the eye is minimized.

2 Claims, 4 Drawing Sheets

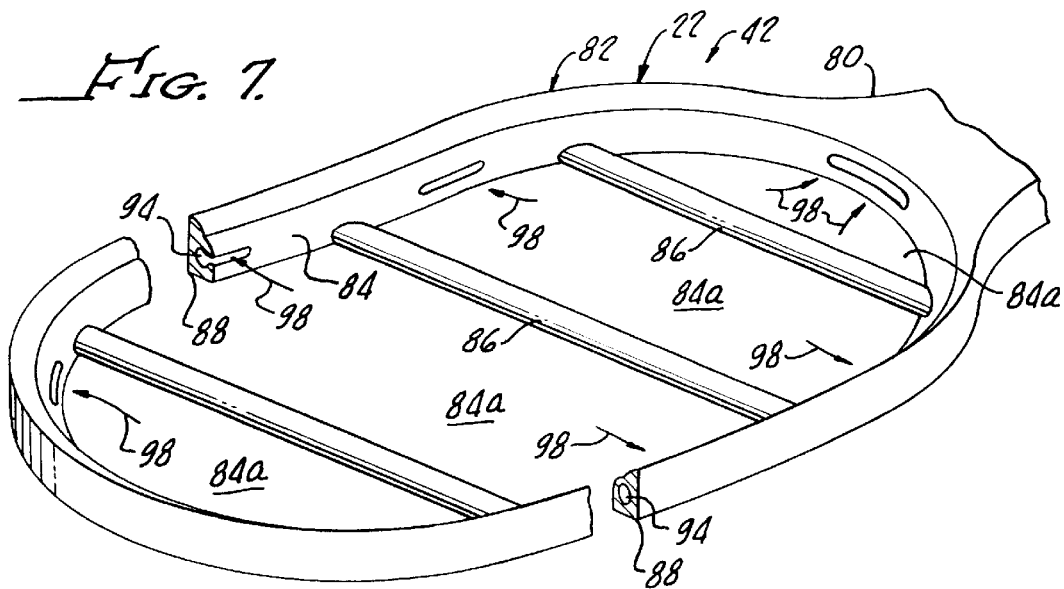
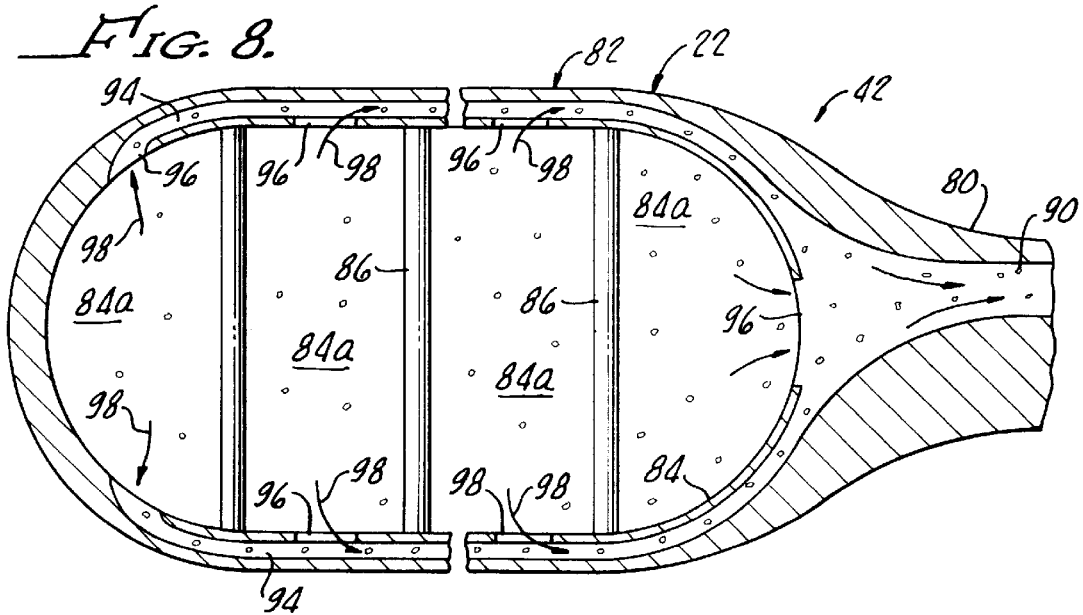
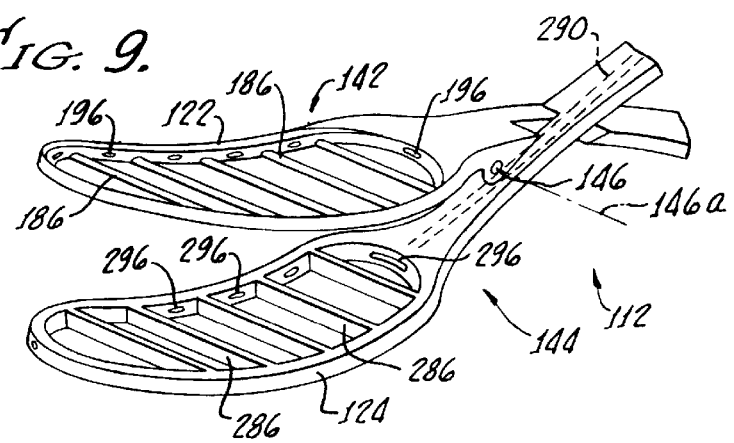

OPHTHALMIC INSTRUMENT FOR CATARACT SURGERY

BACKGROUND OF THE INVENTION

1. Field of the Invention

The present invention relates to ophthalmic instruments for use in cataract surgery. More particularly, the invention relates to an instrument which is usable to remove the natural lens from the eye, and which may also provide irrigation to the eye and aspiration of irrigation liquid and fragments of the fractured natural lens during surgery.

2. Related Technology

During ophthalmic surgery, it is often necessary to perform various functions within the eye. For example, during cataract surgery, these functions include breaking up of the natural lens of the eye, irrigating the eye and aspirating the natural lens particles and irrigation liquid from the eye.

A conventional device for breaking up the natural cataractogenious lens is a phacoemulsifier. This device uses a tubular cutting tip vibrated by ultrasonic energy and centrally provided with vacuum aspiration to remove the natural lens in fragments. However, the conventional phacoemulsifier has a significant risk of damage to surrounding eye tissues because of the vigor of its action.

To carry out surgical procedures within the eye, it is necessary to make one or more incisions in the eye. To minimize trauma and to speed the healing process, it is desirable that the incisions be as small as possible. The ophthalmic instruments are then inserted through the incisions into the interior of the eye. Once inserted, it is desirable to limit movement of the instruments at the sclera and the posterior capsule to calm the eye. Unfortunately, restricting movement of the instruments within the eye is often inconsistent with the task that the surgical instruments must perform. In addition, the function to be performed may require movement of the tip of the instrument (such as the cutting and aspirating tip of the phacoemulsifier) to various different locations in the eye, some of which are relatively inaccessible. Because of the vigorous action of the conventional phacoemulsifier, surrounding eye tissues which may be inadvertently contacted by this tip during movements of the instrument in the eye are at risk of damage or destruction.

It would be desirable to provide ophthalmic surgeons with an instrument capable of easily removing the natural cataractogenious lens via a small incision, but which is easier to control and less likely to do damage to surrounding tissues than the conventional phacoemulsifier.

SUMMARY OF THE INVENTION

In view of the deficiencies of the conventional technology, it is an object for this invention to provide an ophthalmic instrument which avoids one or more of these deficiencies.

Another object for this invention is to provide an ophthalmic instrument which can be inserted through a small incision into the eye and, once inserted, can perform various functions associated with the removal of the natural cataractogenious lens.

Further, it is an object to provide such an instrument which is configured so that work can be performed at various different locations within the anterior capsule of the eye with only minimal movement of the portion of the instrument which contacts the cornea or sclera.

An advantage of an ophthalmic instrument according to the present invention is that necessary functions can be performed through a small incision, and the eye is allowed to remain more calm. In addition, because the small incision may fit relatively tightly around the instrument, fluid loss from the eye is minimized.

The invention can be embodied in an ophthalmic instrument for breaking up the natural cataractogenious lens which includes a pair of crossed and pivotally interconnecting branches each defining at a distal end portion of the instrument a respective one of a pair of opposed jaw portions, the pair of branches in a proximal portion of the instrument each defining a respective handle section; the pair of jaw portions being paddle-like and opposing one another in face-to-face confrontation, the pair of jaw portions defining an edge engageable with a natural lens to remove a portion thereof; and at least one jaw portion of the pair of jaw portions being perforate to define an aperture at which a removed portion of natural lens may be further fragmented by cooperative opposing action of the other of the pair of jaw portions.

The ophthalmic instrument also may include at least one of the pair of branches on a proximal portion thereof defining a nipple for connection with one of a source of irrigating liquid and a source of aspirating vacuum. The one branch defines an internal passage communicating with the nipple and opening outwardly on the respective one of the pair of jaw portions.

This construction of an ophthalmic instrument embodying the present invention provides a number of advantages. For example, the natural lens may be fragmented and reduced to particles which are irrigated and aspirated from the eye with minimal trauma to surrounding tissues.

An important feature of the invention is that a stem portion of the instrument which changes little in response to manipulation of the jaws is received in the incision and minimizes fluid loss from the eye. The pivot for the pair of jaws is disposed in this transition section.

This enables the supply of an irrigation fluid through the second proximal opening to the interior of an eye.

Flexible conduits may be employed to couple the proximal openings of the instrument to a vacuum aspiration source and to a source of irrigation liquid.

The invention, together with additional features and advantages thereof, may best be understood by reference to the following description taken in connection with the accompanying illustrative drawings.

BRIEF DESCRIPTION OF THE DRAWING FIGURES

FIG. 7 is a still more greatly enlarged fragmentary perspective view of one portion of an instrument according to the present invention, which portion was seen in FIG. 5; with the portion shown broken away from the remainder of the instrument for clarity of illustration;

FIG. 8 is a fragmentary cross sectional view of the portion seen in FIG. 7; and

Figure 5:
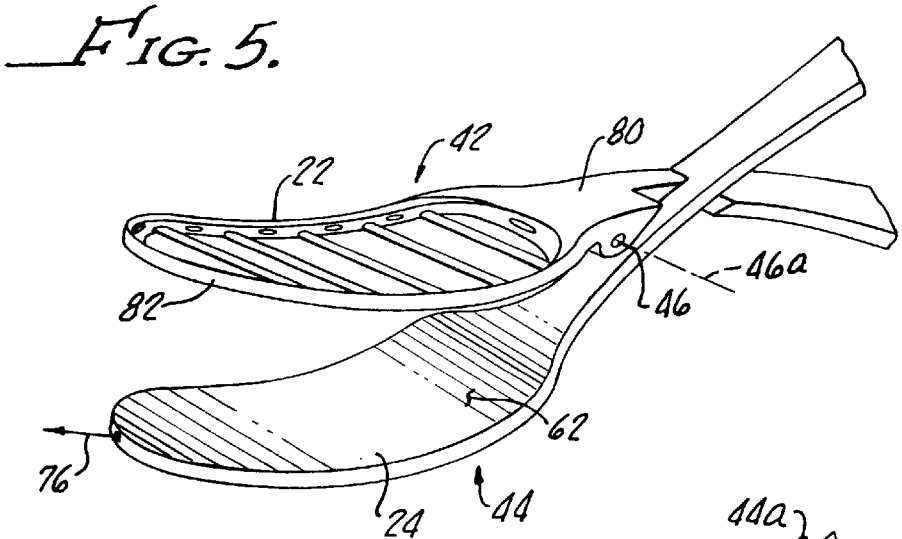
FIG. 5 is a greatly enlarged fragmentary perspective view of a portion of an instrument according to the present invention.

FIG. 9 provides a fragmentary perspective view similar to FIG. 5, but depicting an alternative embodiment of the invention.

DETAILED DESCRIPTION OF EXEMPLARY PREFERRED EMBODIMENTS OF THE INVENTION

In a cataract condition, the natural lens of the eye becomes hardened and cloudy. This natural lens must be removed to allow an intraocular lens to be inserted into the posterior chamber of the eye behind the iris, thus restoring vision to the patient. Typically, the hardening of the lens begins at the center, or cortex of the lens. To remove the natural lens of the eye, the central hard material is first removed, leaving the softer peripheral portions of the natural lens within the capsular bag. The surrounding softer material is then removed.

Figure 1:
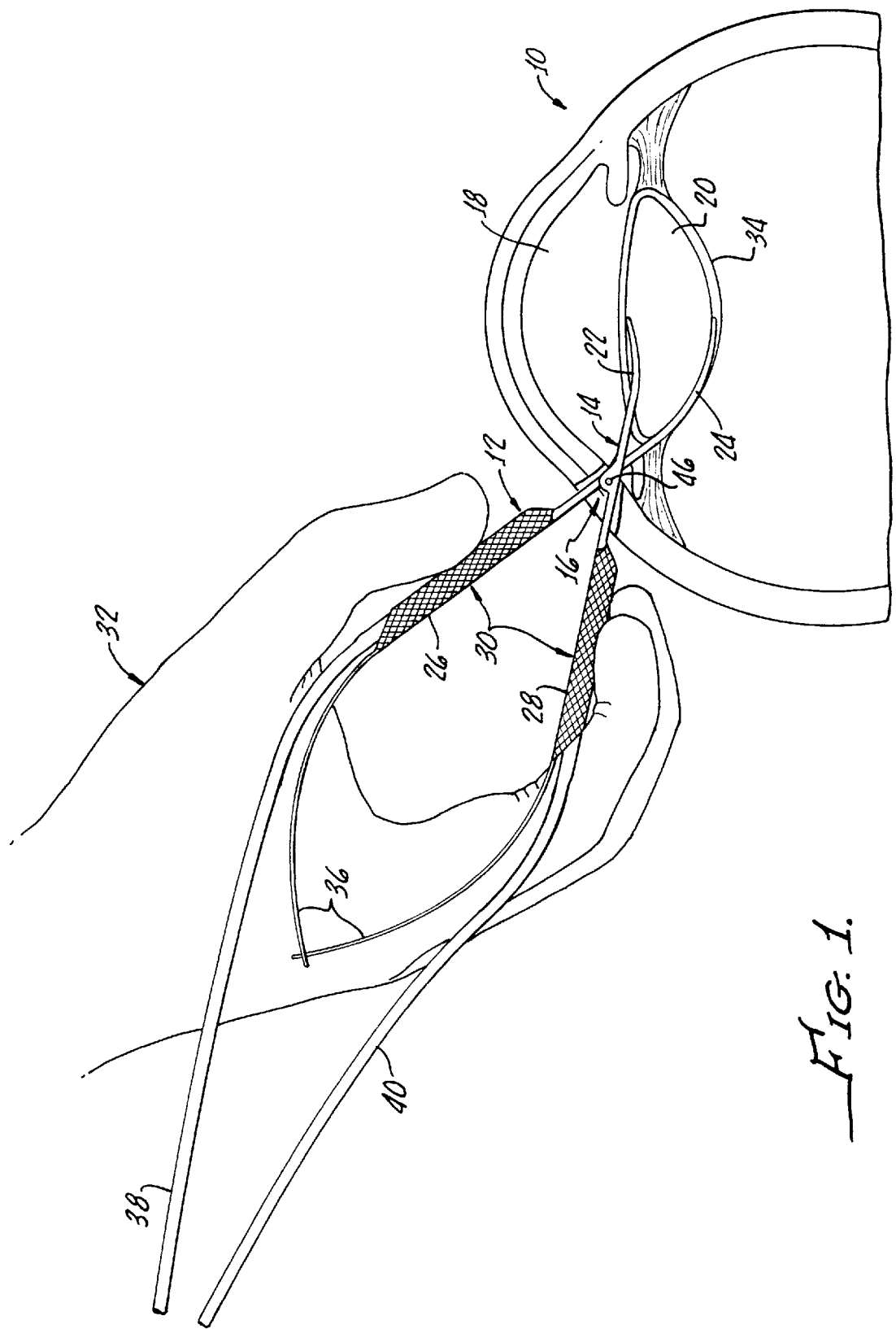
FIG. 1 is a diagrammatic elevational view, partially in cross section, illustrating an ophthalmic instrument constructed in accordance with the teachings of this invention being employed to remove the cataractogenious natural lens within an eye; which eye for clarity of illustration is depicted at an enlarged scale compared to the instrument.

Viewing FIG. 1, a human eye 10 is shown in fragmentary cross sectional view and at an enlarged size for clarity of illustration. A forceps-like ophthalmic instrument 12 according to the present invention is inserted at a distal end portion 14 thereof via a small (preferably 3 mm) incision 16 adjacent to the junction of the cornea and sclera into the anterior chamber 18 of the eye for cataract surgery to remove the natural lens 20. As will be seen further, the instrument 12 includes a pair of opposed somewhat paddle-shaped jaw portions 22, 24 which in conjunction with one another may be manipulated through the dilated iris of the eye 10. The jaw portions are manipulated by coordinated manual movements of a pair of opposed handles 26, 28 of a proximal portion 30 the instrument (i.e., by a surgeon whose hand is indicated with numeral 32). The coordinated movements of the jaws 22, 24 are effective to fracture the lens 20 into particles. The particles of the fractured lens 20 are then removed from the posterior chamber 34 and anterior chamber 18, allowing subsequent placement of an intraocular lens into the posterior chamber 34 of the eye behind the iris.

Figure 2:
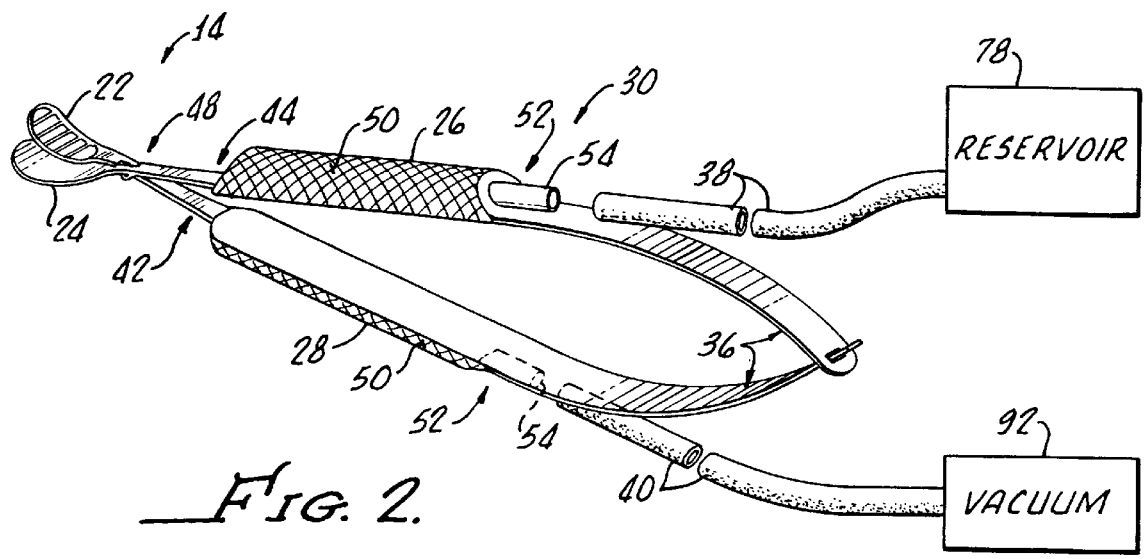
FIG. 2 is a perspective view of the instrument according to the present invention.
Figure 4:
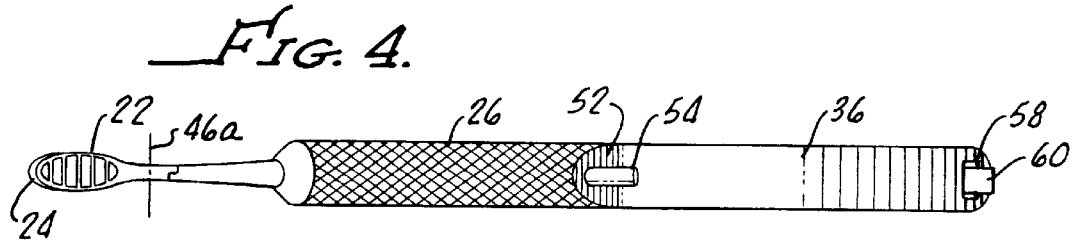
FIG. 4 is a side elevation view of the instrument according to the present invention.
Figure 3:
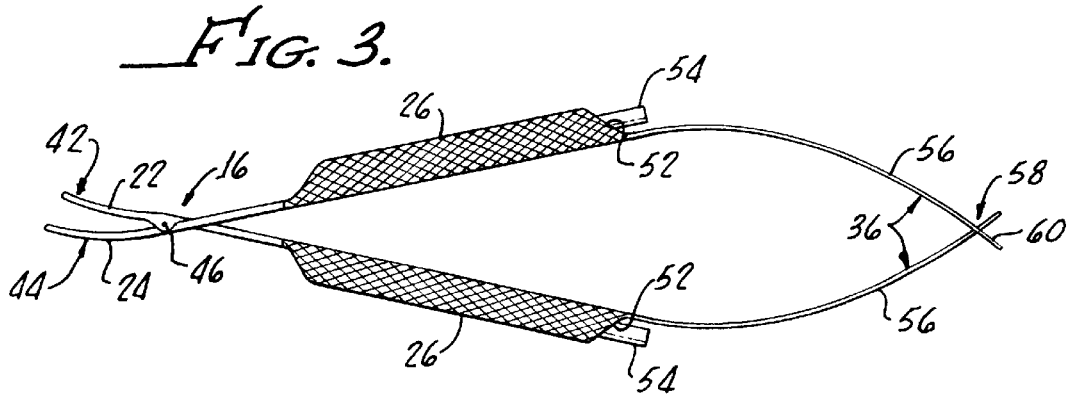
FIG. 3 is a plan view of the instrument according to the present invention.

As will be seen, the instrument 12 includes a resilient spring portion 36 yieldably biasing the jaws 22, 24 apart, and is connected at each of the handles 26, 28, to one of a pair of flexible conduits 38, 40 respectively providing for supply of irrigation liquid into the eye 10, and for aspiration of liquid and particles of the fractured lens 20, both via the instrument 12. FIGS. 2, 3, and 4 viewed in conjunction provide both a perspective view and orthographic views of the instrument 12. This instrument 12 is seen to include a pair of crossed branches 42, 44, which respectively each define one of the jaw portions 22, 24, and one of the handles 26, 28. The branches 42, 44, are crossed and pivotally connected by a pin 46 (best seen in FIG. 3). The pivot pin 46 defines a pivot axis 46a, best seen in FIGS. 4 and 5. A transition portion 48 adjacent and extending a distance on each side of the pivot pin 46 generally defines the demarkation between the distal portion 14 of the instrument which will be inserted into an eye, and the proximal portion 30 which will remain outside of the eye for manual manipulation by surgeon 32.

It is the transition portion 48 which will reside in the incision 16 during surgery and manipulation of the jaws 22, 24 by manual movements of the handles 26, 28. Because the instrument 12 is slim and generally small with rounded exterior surfaces in the transition portion 48, and the incision 16 may fit snugly about this portion of the instrument 12, fluid loss from the eye 10 during surgery is minimized. Further, because the pivot pin 46 is generally central of this transition portion (as can be seen in FIG. 1, for example) opening and closing movements of the jaws 22, 24, and handles 26, 28 disturb the surrounding tissues of the eye only minimally. Further, the movements of the instrument in the transition portion 48 are for the most part along the line of incision 16, which further minimize trauma to eye tissues.

Each of the branches 42, 44 defines a knurled surface section 50 which provides purchase on the handles 26, 28 for manual manipulation by the surgeon 32. Further, more proximally of the knurled surface portions 50, each branch defines a recessed or outwardly concave surface portion 52 at which is disposed a nipple 54 extending along the line of the branch to receive a respective end of one of the conduits 38, 40. The functions of these nipples and flow of irrigation liquid and aspiration will be further described below. Each branch 42, 44, also includes a relatively slender and resilient proximally-extending portion 56, which in its relaxed or undistorted condition is more arcuate (i.e., has a greater curvature) than is seen in the drawing Figures. One of the resilient portions 56 defines an aperture 58, while the other defines a tab 60 pivotally receivable into the aperture 58. Consequently, the resilient portions 56 are forced cooperatively into a more straightened condition, and cooperatively bias the handles 26, 28 apart. This resilience of the portions 56 also biases the jaw portions 22, 24 yieldably apart.

Figure 5A:
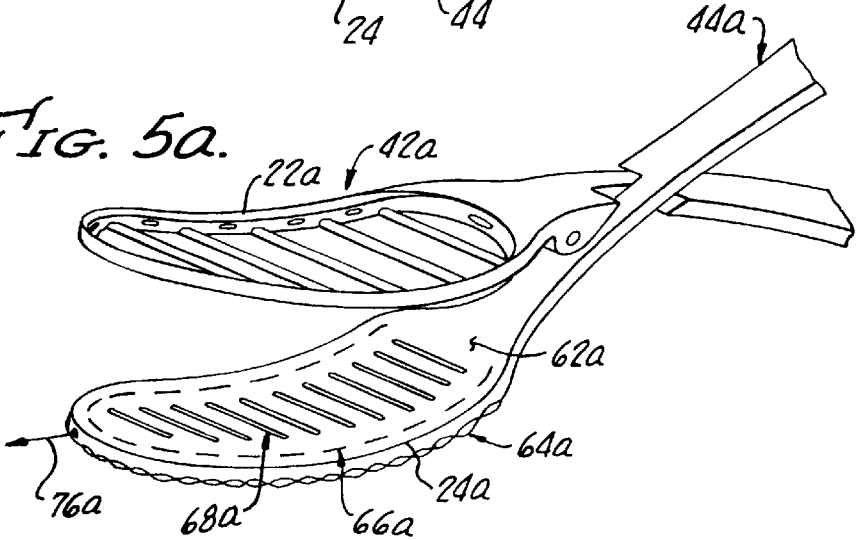
FIG. 5a is a greatly enlarged fragmentary perspective view of one portion of an instrument according to an alternative embodiment of the present invention.

Viewing FIG. 5, an enlarged fragmentary view of the jaw portions 22, 24 is provided. These jaw portions are seen to be somewhat curved when viewed in 2 direction parallel with the pivot pin 46, (i.e., curved in a plane perpendicular to the axis of pin 46) and to be somewhat paddle-shaped and flat in opposition to one another. As is seen in FIG. 5, one of the jaws 24 defines a continuous or non-perforate smooth surface 62. As is indicated in FIG. 5a, the surface 62 (i.e., 62a in the alternative embodiment) with arrows 64, 66, and 68a, the surface 62 may have one or more of: a serrated edge, a striated surface portion, and/or a ribbed surface portion, all with the purpose of assisting in gripping and fracturing the lens 20 into particles.

Figure 6:
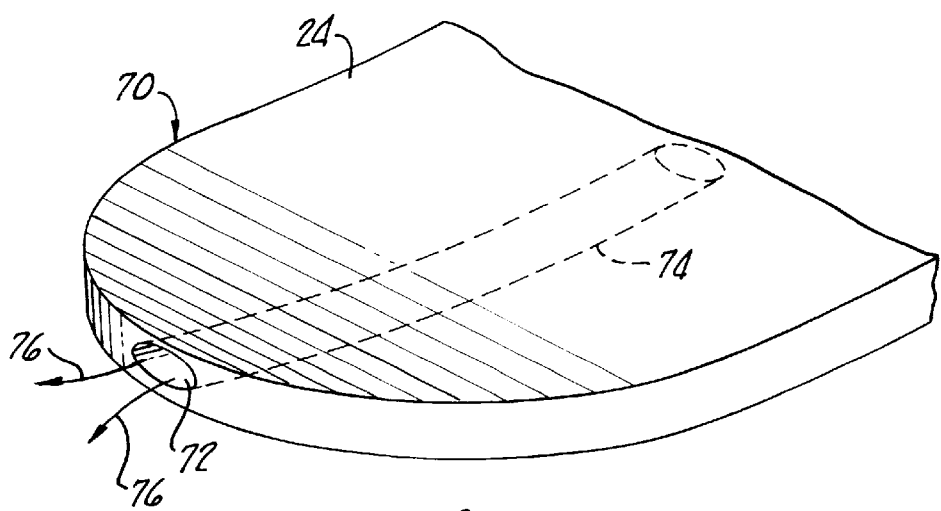
FIG. 6 is a still more greatly enlarged fragmentary perspective view of one portion of an instrument according to the present invention, which portion was seen in FIG. 5.

FIG. 6 illustrates that on an extreme distal end portion 70 of the jaw portion 24, this jaw portion defines an opening 72 communicating with the respective nipple 54 via an internal passage 74 of the branch 44. Thus, irrigation liquid (indicated by flow arrow 76) may be supplied into the eye 10 via the instrument 12 from a source 78 of such liquid (schematically illustrated in FIG. 2). This liquid flow is indicated with arrow 76a in the alternative embodiment of FIG. 5a.

Viewing FIGS. 5, 7, and 8 in conjunction, it is seen that the other jaw 22 of the instrument 12 is paddle-shaped, but is perforate. That is, the jaw 22 includes a delta-shaped or triangle-shaped stem portion 80 supporting a peripheral frame portion 82, which is somewhat wedge-shaped in cross section, viewing FIG. 7. The frame portion 82 opposes jaw portion 24, and defines an opening 84 spanned by several bar portions 86. The bar portions 86 are preferably formed integrally with the frame portion 82, although this is not necessarily the case. The bars 86 divide the opening 84 into plural apertures, each indicated with the numeral 84a, best seen in FIGS. 7 and 8. Further, because the frame portion 82 is wedge-shaped in cross section, it is seen to define a comparatively sharp peripheral edge 88 in opposition to the surface 62 of the jaw 24.

Internally, the branch 42 defines a passage 90 (best seen in FIG. 8) communicating with the respective nipple 54, and via conduit 40 to a source 92 for vacuum aspiration (as is also schematically illustrated in FIG. 2). The passage 90 bifurcates at the stem portion 80 and communicates with a peripheral passage 94 disposed in the frame portion 82. Inwardly of the opening 84 of frame portion 82, this frame portion defines multiple spaced apart openings 96 to the passages 94, and passage 90. Consequently, as is depicted by arrows 98, irrigation liquid delivered via opening 72 along with particles of fractured lens 20 are aspirated via openings 96 and are removed along passages 94, passage 90, and conduit 40.

FIG. 9 is similar to FIG. 5, but fragmentarily depicts another alternative embodiment of the invention. In order to obtain reference numerals for use in describing the alternative embodiment depicted in FIG. 9, features which are the same or analogous in structure or function to those depicted and described above are referenced with the same numeral used above, and increased by one-hundred (100), (or by 200 in order to distinguish duplicated structures from one another). Viewing now FIG. 9, it is seen that an instrument 112 includes a pair of jaws 122 and 124 which are both perforate like jaw 22 of the first embodiment. The jaw 124 defines a passage 290 leading to openings 296 via a bifurcated peripheral passage 294, analogous to that illustrated and described in connection to FIGS. 7 and 8. Accordingly, in this case, irrigation liquid is delivered to the eye via the plural openings 296. The jaw 122 is analogous to jaw 22 described above, and need not be further described, except to point out that the bar portions 186, 286 of the two jaw portions are in opposition to one another to effectively capture therebetween portions of the lens which have been removed during the surgery by gouging and cutting action at the periphery of the jaws 122, 124. Consequently, these removed lens portions can be further fractured into small particles for aspiration via the openings 196. In other respects, the instrument 112 is the same as instrument 12, so that reference hereinafter to instrument 12 in the following description of a surgical procedure will be understood also to refer to instrument 112. Parenthetical references to the numerals used in describing FIG. 9 are included merely as a convenience to the reader.

In use, after the incision 16 is made, the jaws 22, 24 are initially held together manually by the surgeon 32 in order to pass these jaws through the incision 16. The distal portion 14 is passed into the incision. Thus, the distal portion of the instrument 12 is inserted into the anterior chamber 18 of an eye 10, and the surgeon 32 thereafter manipulates the handles 26, 28 to grasp lens 20 (or portions thereof) with jaws 22, 24. The jaws 22, 24 are effective to progressively fragment the lens 20 by gouging, cutting, and fragmenting action. Progressively, the lens 20 is reduced to fragments and to particles (i.e., by action of the frame portion 82 and bar portions 86 with the opposing surface 62 (or 62*a*, with one or more of the optional features 64*a*, 66*a*, or 68*a*) of the other jaw portion 24. Irrigation fluid is supplied by source 78 and opening 72 (or openings 196) during this procedure to assist in moving the fragments and particles to positions for their further reduction or aspiration. In other words, the lens is reduced to fragments, and the fragments to particles which are sufficiently small that they can be removed via the openings 96 (196) and passage 94 (194) to passage 90 (190) and aspiration vacuum source 92. As pointed out above, because the instrument 12 fits snugly in the incision 16, fluid loss from the eye is minimized. Further, the transition portion 48 does not change much in size as the jaws 22, 24 are manipulated by the surgeon 32, so that trauma to the surrounding eye tissues is minimal.

Although exemplary embodiments of the invention have been shown and described, many changes, modifications and substitutions may be made by one having ordinary skill in the art without necessarily departing from the spirit and scope of this invention.

I claim:

1. An ophthalmic instrument for breaking up the natural cataractogenious lens, said instrument comprising:

a pair of crossed and pivotally interconnecting branches each defining at a distal end portion of said instrument a respective one of a pair of opposed jaw portions, said pair of branches in a proximal portion of said instrument each defining a respective handle section;

said pair of jaw portions each being paddle-shape and opposing one another in face-to-face confrontation, each of said pair of jaw portions defining a peripheral edge engageable with opposite surfaces of said natural lens to remove a portion thereof, each of said pair of jaw portions being perforate to define plural apertures, and having a part thereof adjacent to said plural apertures against which a removed portion of said natural lens is further fragmented by cooperative opposing action of the other of said pair of jaw portions.

2. The ophthalmic instrument of claim 1 wherein a pair of apertures separated from one another by a bar portion in one of said pair of jaw portions is effective to fragment said removed portion of said natural lens by cooperative opposing action of the other of said pair of jaw portions.

* * * * *